United States Patent [19]
McKenzie et al.

[11] Patent Number: 5,747,021
[45] Date of Patent: May 5, 1998

[54] AFTER SHAVE TREATMENT COMPOSITION

[76] Inventors: Therman McKenzie, 647 Watson Bay, Stone Mountain, Ga. 30087; James Agard, P.O. Box 2933, Decatur, Ga. 30034

[21] Appl. No.: 780,955

[22] Filed: Jan. 10, 1997

[51] Int. Cl.$^6$ .................................................. A61K 7/15
[52] U.S. Cl. ......................... 424/73; 514/159; 514/724
[58] Field of Search ........................ 424/73; 514/159, 514/724

[56] References Cited

U.S. PATENT DOCUMENTS

| | | | |
|---|---|---|---|
| 3,981,681 | 9/1976 | de la Gusrdia | 8/161 |
| 4,228,163 | 10/1980 | Bliss | 424/240 |
| 4,525,344 | 6/1985 | Tutsky | 424/73 |
| 4,665,063 | 5/1987 | Bar-Shalom | 514/164 |
| 4,775,530 | 10/1988 | Perricone | 424/73 |
| 4,867,967 | 9/1989 | Crutcher | 424/73 |
| 4,944,939 | 7/1990 | Moore | 424/73 |
| 5,034,221 | 7/1991 | Rosen et al. | 424/73 |

OTHER PUBLICATIONS

Windolz et al., *The Merck Index* 10th Ed. abs. nos. 1813 and 7450.

*Primary Examiner*—Kevin E. Weddington
*Attorney, Agent, or Firm*—Jerome J. Norris

[57] ABSTRACT

A topical composition comprising:
 (a) A mixture of water, glycerin and propylene glycol;
 (b) Homopolymer of acrylic acid crosslinked with an allyl ether of pentaerythritol, and allyl ether of sucrose, or an allyl ether of propylene.
 (c) Isopropyl alcohol;
 (d) Acetylsalicylic acid and ethyl alcohol denatured with t-butyl alcohol and a combination of two or three of the following: brucine (alkaloid), brucine sulfate or quassin; and
 (e) Polymer of ethylene oxide that conforms to the formula: $H(OCH_2CH_2)n\ OH$; wherein n has an average value of 8.

8 Claims, No Drawings

AFTER SHAVE TREATMENT COMPOSITION

BACKGROUND OF THE INVENTION

The present invention relates to an after shave treatment composition. More particularly, the present invention relates to an after shave treatment composition useful in treating a skin disorder known as Pseudofolliculitis Barbae. The after shave treatment composition is applied to the face after shaving, for treatment and prevention of Pseudofolliculitis Barbae.

Pseudofolliculitis Barbae is a bacterial disorder, usually caused by staphylococcus aureus, occurring chiefly in the beard of blacks, especially in the submandibular region of the neck, the characteristic lesions being erythematous papules, and sometimes pustules containing buried hairs. This condition is sometimes commonly referred to as "razor bumps".

The prevention of Pseudofolliculitis Barbae has been difficult, despite the fact that it is known that regular shaving that would cut emerging facial hairs at the skin's surface could eliminate the condition by consistently removing hairs before they have an opportunity to grow and re-enter the skin; however, the main disorder or condition of the disorder is the in-growth of facial hairs which have surfaced above the skin and back into the skin at a location in close proximity to the follicle from which the hair initially surfaced.

One solution for prevention of Pseudofolliculitis Barbae is the use of depilatory compositions; however, while this is an effective remedy in achieving removal of the hairs by non-cutting means before they can re-enter the skin, it is unfortunately the case that, for some sufferers, the depilatory itself is an irritant.

Because Pseudofolliculitis Barbae is caused by facial hairs having a tendency to greatly curve, a greater incidence of this condition occurs in the Black race.

Some prior art compositions or methods directed to the treatment of Pseudofolliculitis Barbae are discussed in U.S. Pat. Nos. 3,981,681; 4,228,163; 4,525,344; 4,775,530; and 5,034,221.

Another group of prior art references directed to anti-inflammation compositions are described in U.S. Pat. Nos. 4,219,548; 4,364,940; and 4,665,063. These latter group of references are especially directed to processes for treating acne and utilize in one form or another, acetylsalicylic acid; however, the dermatology condition of acne is appreciably different from Pseudofolliculitis Barbae in that, while acne is an inflammatory disease of the pilosebaceous unit, and involves the sebaceous or oil glands of the skin, Pseudofolliculitis Barbae does not generally involve the sebaceous glands. Instead, Pseudofolliculitis Barbae is caused by the in-growth of facial hair which has previously surfaced from the skin and has strongly curved back into the skin, proximate the follicle from which the hair initially surfaced.

More specifically, U.S. Pat. No. 4,665,063, in one of its embodiments, utilizes a composition which is a combination of acetylsalicylic acid and isopropyl alcohol to treat psoriasis and seborrhea. Psoriasis and Seborrhea are dermatological disorders not related to Pseudofolliculitis Barbae, as Seborrhea and Psoriasis are commonly characterized by lesions of the skin that are of the crusting and flaking type, and these crusting and flaking type lesions of the skin are not present in the disorder known as Pseudofolliculitis Barbae. Further, Seborrhea and Psoriasis are generally not limited to the facial skin, as is the condition of Pseudofolliculitis Barbae.

Further still, although the process or cause of action of Pseudofolliculitis Barbae is generally well known, the causation factors of Seborrhea and Psoriasis are not.

SUMMARY OF THE INVENTION

The present invention comprises an after shave treatment composition and method of delivering the active ingredient of this composition to the skin after shaving as a transparent composition comprising isopropyl alcohol, SD 40 ethanol, acetylsalicylic acid, carbomer, propylene glycol, glycerin, PEG-8, and deionized water. The aftershave treatment composition of the invention is applied daily after using a razor, depilatory or electric razor, in order to kill bacteria and reduce inflammation throughout the course of the day. Further, the concentrated aftershave treatment composition of the invention helps improve the overall condition of the skin.

One object of the present invention is to provide an after shave treatment composition for treatment of Pseudofolliculitis Barbae.

Another object of the invention is to provide an after shave treatment composition for treatment of Pseudofolliculitis Barbae comprising isopropyl alcohol, SD ALCOHOL 40, acetylsalicylic acid, Carbomer, propylene glycol, glycerin, PEG-8, and deionized water.

A yet further object of the invention is to provide an after shave treatment composition for treatment of Pseudofolliculitis Barbae characterized by sufficient viscosity to enable the after shave treatment composition to remain on the face for a sufficient period of time to enable the therapeutic ingredients to work, and yet eliminate the tendency of the treatment composition to impart a "chalky" appearance in contrast to the dark or ebony skin complexion of African Americans or members of the Black race who would use the composition.

A still further object of the invention is to provide a transparent or see through after shave composition for treatment of Pseudofolliculitis Barbae comprising the following composition:

| INGREDIENT |
| --- |
| ISOPROPYL ALCOHOL |
| SD ALCOHOL 40[1] |
| ACETYLSALICYLIC ACID |
| CARBOMER[2] |
| PROPYLENE GLYCOL |
| GLYCERIN[3] |
| PEG-8 |
| (Polymer of ethylene oxide that conforms to the formula: H(OCH$_2$CH$_2$)n OH) |
| where n has an average value of 8 |
| DEIONIZED WATER |

[1]Ethyl alcohol denatured with t-butyl alcohol and a combination of two or three of the following: brucine (alkaloid), brucine sulfate or quassin.
[2]Homopolymer of acrylic acid crosslinked with an allyl ether of pentaerythritol, and allyl ether of sucrose, or an allyl ether of propylene.
[3]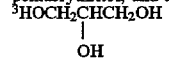

The foregoing and other objects and advantages of the invention will become apparent from the more detailed description of the invention.

DETAILED DESCRIPTION OF THE INVENTION

The after shave treatment composition of the invention results from the combination of: ISOPROPYL ALCOHOL;

SD ALCOHOL 40; ACETYLSALICYLIC ACID; CARBOMER; PROPYLENE GLYCOL; GLYCERIN; PEG-8; and DEIONIZED WATER.

EXAMPLE

Deionized water, glycerin, and propylene glycol are added in a main manufacturing kettle with vigorous mixing at ambient temperature, whereupon CARBOMER is added with vigorous stirring, until all of the CARBOMER is added; approximately 0.1% of sodium hydroxide, or aqueous ammonia is then added to hydrate and thicken the resulting slurry; thereafter, the stirring or agitation is reduced to medium speed, whereupon isopropyl alcohol is added very slowly.

Using a different or side kettle, acetylsalicylic acid is slurried with SD ALCOHOL 40 at ambient temperature while increasing the speed of the mixture in the main kettle; thereafter, the aspirin or acetylsalicylic acid / SD ALCOHOL 40 slurry is added to the main batch with stirring, and stirring is continued until the batch becomes transparent or clear (which is an indication that the mixture is homogeneous); thereafter, PEG-8 is added, and if desired, a fragrance such as chamomile is added to obtain the after shave treatment composition.

While it has been found that an after shave composition containing the ingredients isopropyl alcohol, SD ALCOHOL 40, acetylsalicylic acid, CARBOMER, propylene glycol, glycerin, PEG-8, and deionized water is effective for treating the skin disorder Pseudofolliculitis Barbae, the composition leaves a "chalky", white or ashen film residue on the skin and is of a viscosity such that the composition will not remain on skin for sufficient lengths of time to maximize the efficaciousness of acetylsalicylic acid in combating Pseudofolliculitis Barbae for 24 hours or an entire day. However, it has been found that the after shave treatment composition of the invention is useful in treating the skin disorder Pseudofolliculitis Barbae without leaving an "chalky", white film or ashen residue on the skin if the composition is kept transparent or clear by keeping the ingredients, preferably, within the following ranges:

| INGREDIENT | WEIGHT PERCENT RANGE |
| --- | --- |
| A) ISOPROPYL ALCOHOL | 30–70 |
| B) SD ALCOHOL 40 | 10–30 |
| C) ACETYLSALICYLIC ACID | 8–22 |
| D) CARBOMER | 0.25–1.75 |
| E) PROPYLENE GLYCOL | 2–15 |
| F) GLYCERIN | 2–15 |
| G) PEG-8 (Polymer of ethylene oxide that conforms to the formula: H(OCH$_2$CH$_2$)n OH) where n has an average value of 8 | 1–8 |
| H) DEIONIZED WATER | - Balance to 100 |

This preferred range of ingredients provides an after shave composition having a viscosity of between about 250 to about 500 cps, and at this viscosity range, the composition remains intact on the face and renders acetylsalicylic acid efficacious for 24 hours in combating Pseudofolliculitis Barbae when applied evenly over the skin once a day and not rinsed off until night time or immediately prior to going to bed.

While the composition is effective as an after shave treatment composition that is useful in treating the skin disorder known as Pseudofolliculitis Barbae outside of the ranges set forth above, it has been found that the composition is only cosmetically acceptable to the user if it can be used without leaving an off-color or ashen appearance on the face of the user (as a result of the transparency of the composition before use and after drying on the face).

While not wishing to be bound by any particular theory as to how the after shave treatment composition or any ingredient therein works, it is nevertheless believed that the ingredients function as hereafter described.

The cosmetic function provided by the CARBOMER is that of building viscosity, and providing "cushion" upon applying the after shave treatment product to the face.

The SD ALCOHOL 40 is a solvent which is safe for use on the skin but at the same time dissolves aspirin sufficiently in order to render the aspirin effective as an anti-inflammatory agent without leaving a remnant "chalky" white film on the face of the user after the evaporative ingredients in the after shave treatment product has dissipated.

The glycerin functions to retard degradation of aspirin and thereby preserve its anti-inflammatory effect. The PEG-8 provides the cosmetic function of what is known as "slip" and is left on the skin after the evaporative ingredients dissipate, thereby eliminating whitening or the chalky appearance which would result in the absence of the use of PEG-8.

Propylene glycol has the cosmetic effect of cooperating with the PEG-8 to augment "slip", except that the propylene glycol slowly evaporates rather than remaining on the skin as does PEG-8.

The use of the deionized water is necessary to enable the CARBOMER to act as a thickener or viscosity builder, and without the use of the deionized water, the CARBOMER would not function to maximize viscosity to between 250 and about 500 cps for the after shave of the composition.

The after shave treatment composition of the invention may be used by observing the following directions:

1. Shave normally using any preferred method, whether by depilatory, razor blade, or electric shaver;
2. Apply a thin coat of the after shave treatment over the shaven areas of the face and neck;
3. Do not rinse off the after shave treatment composition; and
4. At night, before retiring, wash and rinse the face thoroughly.

It has been found that, in order for the after shave treatment composition product to be effective for a 24 hour period in treating Pseudofolliculitis Barbae, it must not be rinsed off the face during the day.

While the invention has been described with reference to the preferred embodiments, it should be appreciated that the invention may embody other percentages of the ingredients than those specifically shown and described and still be effective for treating the skin disorder, Pseudofolliculitis Barbae. Accordingly, changes or modifications can be made in the after shave treatment composition formulation without departing from the principles of the invention, which are defined in the appended claims.

We claim:

1. A transparent topical agent for treating Pseudofolliculitis Barbae that does not leave a chalky white film upon the skin comprising:

(a) A mixture of deionized water, glycerin and propylene glycol;
    (b) Homopolymer of acrylic acid crosslinked with an allyl ether of pentaerythritol, and allyl ether of sucrose, or an allyl ether of propylene;

(c) Isopropyl alcohol;

(d) Acetylsalicylic acid and ethyl alcohol denatured with t-butyl alcohol and a combination of two or three of the following: brucine (alkaloid), brucine sulfate or quassin; and (e) Polymer of ethylene oxide that conforms to the formula: $H(OCH_2CH_2)n\ OH$ wherein n has an average value of 8; said topical agent having a viscocity of between 250 to about 500 cps.

2. A process for producing a transparent after shave composition for treatment of Pseudofolliculitis Barbae that does not leave a chalky white film upon the skin comprising:

(a) Combining deionized water, glycerin and propylene glycol to form a mixture;

(b) Adding a homopolymer of acrylic acid crosslinked with an allyl ether of pentaerythritol, an allyl ether of sucrose, or an allyl ether of propylene while mixing to the mixture of (a);

(c) Adding isopropyl alcohol to the mixtures of (a) and (b);

(d) Forming a slurry of acetylsalicylic acid with ethyl alcohol denatured with t-butyl alcohol and a combination of two or three of the following: brucine (alkaloid), brucine sulfate or quassin, adding the mixture of acetylsalicylic acid and ethyl alcohol denatured with t-butyl alcohol and a combination of two or three of the following: brucine (alkaloid), brucine sulfate or quassin to the mixture of (a), (b) and (c) with stirring until a transparent and homogeneous mixture is formed; and (e) adding a polymer of ethylene oxide that conforms to the formula: $H(OCH_2CH_2)n\ OH$ to the mixture of (a), (b), (c) and (d) to obtain a viscous transparent after shave treatment composition having a viscosity of between about 250 to about 500 cps; wherein n has an average value of 8.

3. The composition of claim 1, in which said homopolymer of acrylic acid crosslinked with an allyl ether or pentaerythritol, and allyl ether or sucrose, or an allyl ether of propylene is present in a weight percent of at least 0.25.

4. The composition of claim 1 wherein said isopropyl alcohol is present in a weight percent of at least 30%.

5. A method for treating Pseudofolliculitis Barbae comprising applying to the affected area of the skin, an effective amount of the composition of claim 1 to provide local relief from irritation due to Pseudofolliculitis Barbae.

6. The method according to claim 5 wherein the said composition comprises a cosmetically acceptable preparation selected from soap, gel, shaving foam, solution, creme, ointment, lotion and stick.

7. The composition of claim 1, wherein weight percent ranges are as follows:

| INGREDIENT | WEIGHT PERCENT RANGE |
| --- | --- |
| A) ISOPROPYL ALCOHOL | 30–70 |
| B) SD ALCOHOL 40 | 10–30 |
| C) ACETYLSALICYLIC ACID | 8–22 |
| D) CARBOMER | 0.25–1.75 |
| E) PROPYLENE GLYCOL | 2–15 |
| F) GLYCERIN | 2–15 |
| G) PEG (Polymer of ethylene oxide that conforms to the formula: $H(OCH_2CH_2)n\ OH$) where n has an average value of 8 | 1–8 |
| H) DEIONIZED WATER | - Balance to 100. |

8. A method for treating Pseudofolliculitis Barbae comprising applying an effective amount of the composition of claim 7 to the face to provide relief from irritation due to Pseudofolliculitis Barbae.

* * * * *